US 9,784,717 B2

United States Patent
Memering et al.

(10) Patent No.: US 9,784,717 B2
(45) Date of Patent: Oct. 10, 2017

(54) ACOUSTIC TESTING OF SAPPHIRE COMPONENTS FOR ELECTRONIC DEVICES

(71) Applicant: Apple Inc., Cupertino, CA (US)

(72) Inventors: Dale N. Memering, Cupertino, CA (US); Matthew Rogers, Cupertino, CA (US); Theodore A. Waniuk, Cupertino, CA (US)

(73) Assignee: APPLE INC., Cupertino, CA (US)

( * ) Notice: Subject to any disclaimer, the term of this patent is extended or adjusted under 35 U.S.C. 154(b) by 476 days.

(21) Appl. No.: 14/462,092

(22) Filed: Aug. 18, 2014

(65) Prior Publication Data

US 2015/0089792 A1    Apr. 2, 2015

Related U.S. Application Data

(60) Provisional application No. 61/884,351, filed on Sep. 30, 2013.

(51) Int. Cl.
*G01R 31/28* (2006.01)
*G01N 29/04* (2006.01)

(52) U.S. Cl.
CPC ... *G01N 29/041* (2013.01); *G01N 2291/0232* (2013.01); *G01N 2291/0289* (2013.01);
(Continued)

(58) Field of Classification Search
CPC .................. G01N 29/041; G01N 3/60; G01N 2291/0289; G01N 2291/101;
(Continued)

(56) References Cited

U.S. PATENT DOCUMENTS 5,892,157 A * 4/1999 Syre .......................... G01L 5/10
73/812
6,424,137 B1 * 7/2002 Sampson .............. B24B 37/013
324/76.21
(Continued)

FOREIGN PATENT DOCUMENTS

CN         1647228      7/2005
CN        203014915     6/2013
(Continued)

OTHER PUBLICATIONS

Gorla et al., "Structural, optical, and surface acoustic wave properties of epitaxial ZnO films grown on (0112) sapphire by metalorganic chemical vapor deposition," Journal of Applied Physics, vol. 85, No. 5, pp. 2594-2602, Mar. 1, 1999.
(Continued)

*Primary Examiner* — Donghai D Nguyen
(74) *Attorney, Agent, or Firm* — Brownstein Hyatt Farber Schreck, LLP

(57) ABSTRACT

In some embodiments, processes for testing for structural flaws in sapphire parts such as display cover plates used in the manufacturing of electronic devices are disclosed. A process may include transmitting a destructive acoustic signal onto a sapphire part, and determining whether the sapphire part failed in response to the destructive signal. The destructive acoustic signal may include a Rayleigh acoustic wave, wherein the destructive acoustic signal breaks the sapphire part if the sapphire part has a surface flaw larger than a specified size. In this manner, only sapphire parts that can withstand the destructive acoustic signal are used in manufacturing of the electronic device.

14 Claims, 3 Drawing Sheets

(52) U.S. Cl.
CPC ............. *G01N 2291/0423* (2013.01); *G01N 2291/101* (2013.01); *G01N 2291/2632* (2013.01); *Y10T 29/49004* (2015.01)

(58) Field of Classification Search
CPC ... G01N 2291/0232; G01N 2291/0423; G01N 2291/2632; G01L 5/10; B24B 37/013; Y10T 29/49004
USPC ............. 29/593; 73/12.08, 812; 324/76.21
See application file for complete search history.

(56) References Cited

U.S. PATENT DOCUMENTS

| | | |
|---|---|---|
| 6,673,478 B2 | 1/2004 | Kato et al. |
| 7,554,654 B2 | 6/2009 | Meeks et al. |
| 7,861,573 B1 * | 1/2011 | Tenaglia .................. G01N 3/60 73/12.08 |
| 2013/0237402 A1 | 9/2013 | Wang et al. |
| 2015/0226723 A1 | 8/2015 | Memering et al. |
| 2017/0089818 A1 | 3/2017 | Bartlow et al. |

FOREIGN PATENT DOCUMENTS

| | | |
|---|---|---|
| JP | H02118615 | 5/1990 |
| JP | H04109709 | 4/1992 |
| JP | H10326385 | 12/1998 |

OTHER PUBLICATIONS

Wang et al., "Experimental study on ultrasonic crushing brazed diamond grits," Superhard Materials Engineering, vol. 23, No. 3, pp. 6-10, Jun. 30, 2011.

* cited by examiner

ACOUSTIC TESTING OF SAPPHIRE COMPONENTS FOR ELECTRONIC DEVICES

CROSS-REFERENCE TO RELATED APPLICATION

This application is a nonprovisional of and claims the benefit to U.S. Provisional Patent Application No. 61/884,351, filed Sep. 30, 2013 and titled "ACOUSTIC TESTING OF SAPPHIRE COMPONENTS FOR ELECTRONIC DEVICES," the disclosure of which is hereby incorporated herein by reference in its entirety.

TECHNICAL FIELD

The present disclosure relates generally to methods for testing of components in electronic devices, and more particularly relates to testing of cover plates or surfaces made of sapphire during the manufacturing of electronic devices.

BACKGROUND

Electronic devices—such as mobile devices, mobile phones, tablet computers, music and multi-media players, watches, gaming devices, and other handheld, wearable or portable devices—have traditionally been formed using glass components such as glass cover plates for surfaces such as touch screens, displays, camera lens covers and buttons.

During manufacturing of such mobile devices, testing of the glass components or parts typically involves mechanical testing including some type of flexural strength test (e.g., a ring on ring flex test, or a three-quarter point bend test). Some limitations of this type of conventional testing include: the glass part is typically loaded with a hard fixture material (e.g., tool steel) to apply the test load; the area being tested on the glass part is typically limited; the stress distribution of a flexural test can be highly non-uniform (with large load peaks existing under the loading locations); and/or the glass part can be weakened by the test, for instance a flaw on the part can grow in size as a result of the testing.

Recently, other materials are being developed for use in place of glass components for use in mobile devices. As recognized by the present inventors, what is needed are improved testing processes and systems that can be used for testing components made of materials other than glass.

SUMMARY

According to one broad aspect of one embodiment of the present disclosure, a process for testing for structural flaws in sapphire parts used in the manufacturing of electronic devices is discussed herein. In one example, the process may include transmitting a destructive acoustic signal onto a sapphire part, and determining whether the sapphire part mechanically failed in response to the destructive signal. In one example, the destructive acoustic signal includes a Rayleigh wave, and the destructive acoustic signal breaks the sapphire part if the sapphire part has a surface flaw. In this manner, only sapphire parts that can withstand the destructive acoustic signal are used in manufacturing of the electronic device.

In another embodiment, if the determining operation determines that the sapphire part mechanically failed, the sapphire part is discarded. In one embodiment, the sapphire part may be a cover plate for a display or touch screen of the electronic device. The electronic device may be a mobile phone, a tablet device, a music player, a multi-media player, a watch, a gaming device, or a handheld, wearable or portable device.

According to another broad aspect of another embodiment of the present disclosure, a process for manufacturing an electronic device is disclosed herein. The process may include the operations of generating and transmitting a destructive acoustic signal onto a sapphire part, determining whether the sapphire part failed in response to the destructive signal, and if the sapphire part did not fail, forming the electronic device using the sapphire part.

According to another broad aspect of another embodiment of the present disclosure, a system for use in manufacturing an electronic device is disclosed herein. In one example, the system may include a transmitter configured to transmit a destructive signal onto a sapphire part, wherein if the sapphire part has a flaw in the surface, the sapphire part breaks in response to the destructive signal thereby eliminating the sapphire part from use in manufacturing the electronic device. The destructive signal may include Rayleigh acoustic waves.

Other embodiments of the disclosure are described herein. The features, utilities and advantages of various embodiments of this disclosure will be apparent from the following more particular description of embodiments as illustrated in the accompanying drawings.

BRIEF DESCRIPTION OF THE FIGURES

The disclosure will be readily understood by the following detailed description in conjunction with the accompanying drawings, wherein like reference numerals designate like structural elements, and in which.

Figure 1:
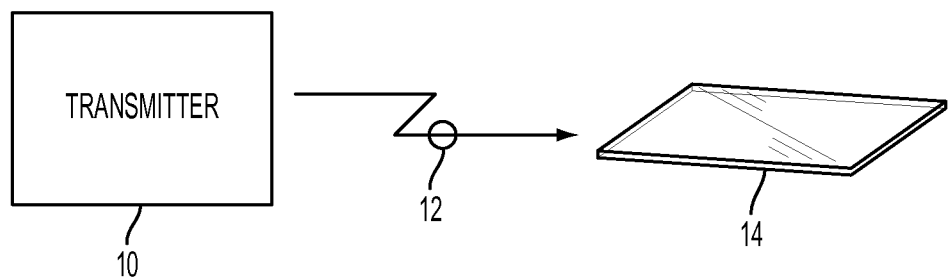
FIG. 1 illustrates an example of a block diagram of a system for testing sapphire parts of an electronic device, in accordance with one embodiment of the present disclosure.

It is noted that the drawings of the invention are not necessarily to scale. The drawings are intended to depict only typical aspects of the invention, and therefore should not be considered as limiting the scope of the invention. In the drawings, like numbering represents like elements between the drawings.

DETAILED DESCRIPTION

Disclosed herein are various embodiments of a process and system for acoustic testing for structural flaws in sapphire parts or components for use in the manufacturing of electronic devices. The processes and systems described herein are useful for testing sapphire parts—such as display cover plates, buttons, camera lens covers—because, as the present inventors have recognized, the strength of a sapphire component is very sensitive to the presence and geometry (size, shape) of surface flaws. The production process of sapphire components can leave a distribution of flaws on a finished surface, but due to the size of the flaws (typically sub-micron or larger), inspecting for and detecting these flaws is extremely difficult. In one example of the disclosure, a testing process or system creates and transmits Rayleigh acoustic waves onto a sapphire part under test which propagate primarily along the surface of the part, such that the part will fracture should a surface flaw of sufficient size be present in the sapphire part under test. In this manner, only sapphire parts without surface structural flaws of a specified size or larger will successfully pass the testing process. Various embodiments of the present disclosure are described herein.

The following detailed description refers to the accompanying drawings that depict various details of examples selected to show how particular embodiments may be implemented. The discussion herein addresses various examples of the inventive subject matter at least partially in reference to these drawings and describes the depicted embodiments in sufficient detail to enable those skilled in the art to practice the embodiments. Many other embodiments may be utilized for practicing the subject matter other than the illustrative examples discussed herein, and many structural and operational changes in addition to the alternatives specifically discussed herein, may be made without departing from the scope of the disclosed subject matter.

In this description, references to "one embodiment" or "an embodiment," or to "one example" or "an example" mean that the feature being referred to is, or may be, included in at least one embodiment or example of the disclosure. Separate references to "an embodiment" or "one embodiment" or to "one example" or "an example" in this description are not intended to necessarily refer to the same embodiment or example; however, neither are such embodiments mutually exclusive, unless so stated or as will be readily apparent to those of ordinary skill in the art having the benefit of this disclosure. Thus, the present disclosure includes a variety of combinations and/or integrations of the embodiments and examples described herein, as well as further embodiments and examples as defined within the scope of all claims based on this disclosure, as well as all legal equivalents of such claims.

Figure 3:
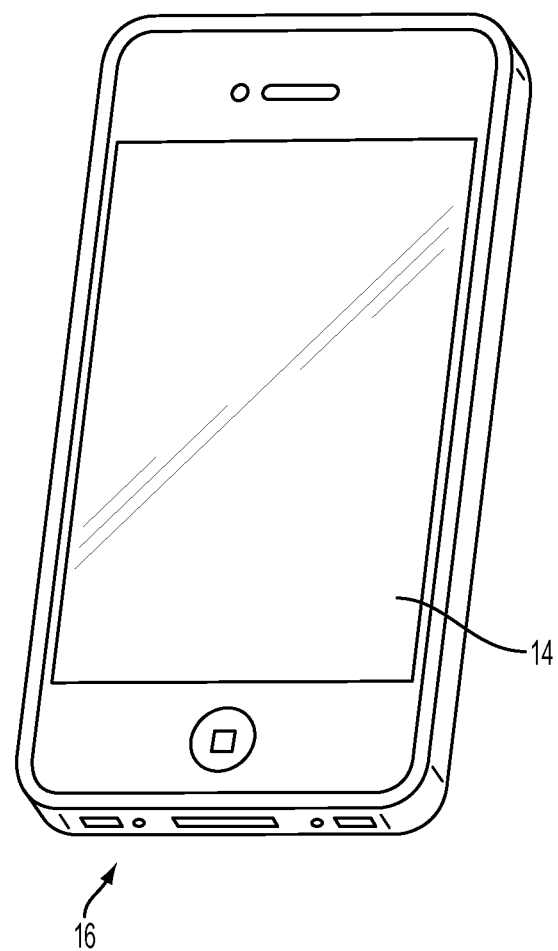
FIG. 3 illustrates an example of an electronic device in the form of a mobile phone having a display cover plate, in accordance with one embodiment of the present disclosure.

FIG. 1 illustrates an example of a block diagram of a system for testing sapphire parts of an electronic device, in accordance with one embodiment of the present disclosure. Referring to FIG. 1, in one example of the disclosure, a surface acoustic wave transmitter 10 generates a destructive signal 12 which is directed to, transmitted onto, imparted onto, or focused at a sapphire part 14 under test. The sapphire part 14 under test may be a sapphire cover plate or surface for use in forming items such as, but not limited to, touch screens, displays, camera lens covers and buttons, for use in electronic devices 16 (FIG. 3) such as, but not limited to, mobile devices, mobile phones, tablet computers, music and multi-media players, watches, gaming devices, and other handheld, wearable or portable devices. FIG. 3 illustrates one example of an electronic device 16 in which embodiments of the invention can be used, in the form of a mobile phone having a display cover plate 14. It is understood that the electronic device in which the sapphire part will be used can take other forms depending upon the implementation.

Referring back to FIG. 1, the transmitter 10 in one example generates and transmits destructive signal 12 in the form of Rayleigh waves which are surface acoustic waves. Rayleigh waves include both longitudinal and transverse energy components that decrease exponentially in amplitude as distance from the surface increases. The transmitter 10 generates the destructive signal 12 having one or more parameters which are selected to destroy, break or crack the part 14 under test if the part 14 has a flaw larger than a specified size.

A specified flaw size will depend on a number of factors, such as the size of the part 14 and the thickness of part 14, as well as the desired strength or robustness of the part 14 as it emerges from the testing process described herein. The robustness of the part 14 may relate to the operational life of the part 14, or the predicted failure time of the part 14 including a flaw. The specified flaw size may be determined on a case-by-case basis depending on how the testing method and system disclosed herein will be used. In one example, acceptable flaw sizes for a given part-under test may be in the sub-micron range (e.g., $0.2\mu$ to $0.8\mu$), and therefore flaw sizes that are larger than sub-micron in size may be considered undesirable for that particular part-under test; hence, the specified flaw size for testing could be, in this example, flaws larger than sub-micron in size. Other tests may be adapted to test parts for other flaw sizes, in accordance with other embodiments of the present disclosure.

In one example of this disclosure, where the destructive signal 12 includes Rayleigh waves generated by a transmitter 10 using a sonic/ultrasonic transducer, a spark driven liquid cavitation, or a laser driven liquid cavitation. The wavelength of the Rayleigh waves generated by a transmitter 10 may be in the range of approximately 50 kilohertz kHz to 2 gigahertz (GHz). The sapphire part under test could be submerged in a liquid or coupled directly to the transmitter 10, with the position or orientation modified for the testing of specific portions of the component. The destructive signal 12 (e.g., Rayleigh waves) would then be directed toward sapphire component 14 relative the positioning and/or orientation of the sapphire component 14. That is, the destructive signal 12 is directed along the surface of the sapphire component 14 under test, passing harmlessly along the component's surface until a flaw of large enough size was encountered by the destructive signal 12, upon which time the flaw in component 14 would be grown to the point of fracture.

The parameters of the destructive signal 12 may include, for instance, amplitude, frequency, wavelength, signal duration, intensity, energy, position, location, or combination thereof, which will destroy, break, or crack the part 14 under test if the part 14 has a flaw, crack, or weakness of a pre-determined, undesirable size.

For sapphire parts 14 which do not have flaws, cracks, or weaknesses larger than a specified size, the destructors signal 12 transmitted by transmitter 10 does not have an adverse effect upon the sapphire part 14.

However, due to the nature of Rayleigh waves in signal 12, if a sapphire part 14 has a flaw, crack, or weakness, the destructive signal 12 will impart energy into the flaw, crack, or weakness in the sapphire part 14 and will grow or increase the size and depth of the flaw, crack, or weakness until the point that the sapphire part will break or otherwise fail if the flaw is greater than the specified size. In this manner, the transmitter 10 can be used to detect structural flaws in sapphire parts 14 having flaws larger than a specified size, so that flawed parts 14 are destroyed and rejected prior to their use in the manufacturing of an electronic device.

It is noted that because the Rayleigh wave destructive signal 12 is adapted to destroy the sapphire part 14 that includes a structural flaw, in one example of this disclosure, a receiver is not provided to detect and measure the signal transmitted by transmitter 10. In another example of this disclosure, an optional receiver may be provided to confirm the proper operation of transmitter 10, wherein the optional receiver detects, measures, and reports the presence and characteristics of destructive signal 12 as transmitted by transmitter 10, thereby confirming the proper operation of transmitter 10 during a testing process.

In one example, destructive signal 12 may be directed at specific portions or regions of the sapphire component 14; for instance, the destructive signal 12 may be directed to regions in the sapphire part 14 that include cut outs or holes in the sapphire component, such as holes for buttons, microphones, cameras, or sensors. In this way, the destructive signal 12 detects whether structural flaws exists within such regions of the sapphire part 14. The signal 12 may be modified for testing of different areas of the components as there may be varying strength requirements in different areas (e.g., outer edges of a part 14 are required to have higher strength than an internal feature edge of part 14, and therefore a test signal 12 applied along an outer edge of a part 14 may be of greater amplitude than a test signal 12 applied on or about an internal feature edge of a part 14).

Figure 2:
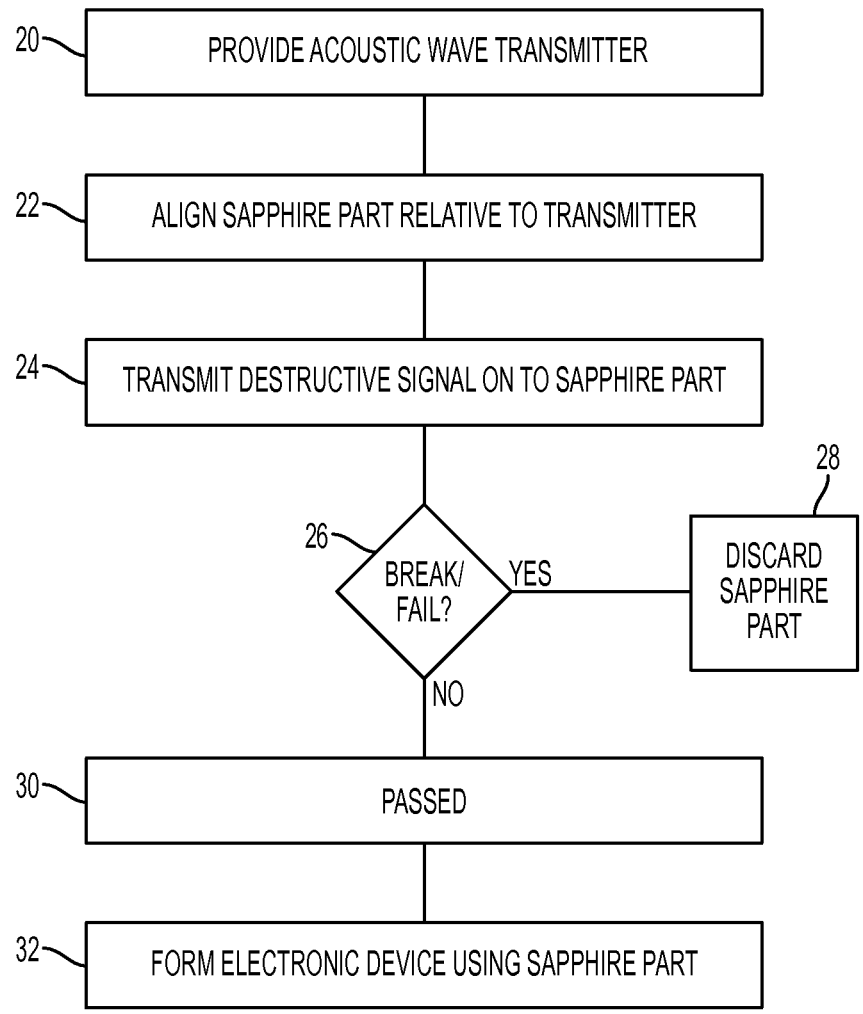
FIG. 2 illustrates an example of a process for testing sapphire parts for use in manufacturing of an electronic device, in accordance with one embodiment of the present disclosure.

FIG. 2 illustrates an example of a process for testing for structural flaws in sapphire parts during the manufacturing of electronic devices, in accordance with one example of the present disclosure.

At operation 20, an acoustic wave transmitter is provided that is capable of generating and transmitting a destructive signal. In one example, the transmitter generates and transmits Rayleigh waves or other surface acoustic waves which have both transverse and longitudinal energy components as the acoustic wave signal travels along a surface.

At operation 22, a sapphire part is positioned or aligned relative to the transmitter provided at operation 20, so that the destructive signal of the transmitter is directed at, transmitted onto, imparted onto, or focused at the sapphire part.

At operation 24, the destructive acoustic wave signals are transmitted onto the sapphire part of operation 22. In one example, operation 24 generates acoustic waves having destructive characteristics of amplitude, frequency, and/or duration such that upon transmission of the signal onto a sapphire part, if the sapphire part has a structural flaw larger than a specified flaw size, which may be in the sub-micron range, the sapphire part will break or otherwise fail.

Operation 26 determines whether the sapphire part broke or otherwise failed as a result of operation 24. In one example, operation 26 includes a visual analysis or inspection of the sapphire part during or after the performance of operation 24.

If operation 26 determines that the sapphire part broke, then control is passed to operation 28 where the sapphire part is rejected as having failed the test. The sapphire part may be discarded or re-worked if the fracture was non-catastrophic.

If operation 26 determines that the sapphire part did not break during or after operation 24, then control is passed to operation 30 where the sapphire part is flagged as having passed this testing process. At operation 32, the sapphire part may be used in the manufacturing or formation of an electronic device. Alternatively, if other or additional testing is desired, or if additional manufacturing processes are to be performed upon sapphire part, such additional testing our manufacturing may take place using the sapphire part.

It can be seen that embodiments of the present disclosure can be utilized to test sapphire parts to a standard or level of consistent strength, despite the fact that there are not simple established strengthening techniques for sapphire parts (such as chemical strengthening which is commonly used for glass parts).

A testing process according to an embodiment of the present disclosure offers advantages over conventional flex strength testing. For instance, the waves of a testing process according to an embodiment of the present disclosure can be highly directional, allowing for focused evaluation of features on the component under test using different test loads. Additionally, the waves of a testing process according to an embodiment of the present disclosure can be in-coupled to the surface of the component under test, without contact from conventionally hard and/or potentially damaging test materials or fixtures. The testing process according to an embodiment of the present disclosure may be more dynamic and realistic than conventional quasi-static flexural strength tests. The testing process according to an embodiment of the present disclosure can be configured to provide uniform control of the test loads across entire component's surface(s).

While embodiments of the present disclosure have been described with reference to sapphire parts and components, it is understood that embodiments of the present disclosure may also be used with other component materials, such as sapphire, glass or other materials as desired. Additionally, although discussed herein a passing a destructive wave along an entire surface of the sapphire part, it is also understood that only a portion of the part may be tested. That is, only a portion of the sapphire part may be exposed to the destructive signal for determining if the sapphire part includes flaws. In a non-limiting example, the edges of the sapphire part may be more prone to flaws than an interior portion. As such, only the edges of the sapphire part may be exposed to the destructive signal when determining if the sapphire part includes a flaw.

While the methods disclosed herein have been described and shown with reference to particular operations performed in a particular order, it will be understood that these operations may be combined, sub-divided, or re-ordered to form equivalent methods without departing from the teachings of the present disclosure. Accordingly, unless specifically indicated herein, the order and grouping of the operations is not a limitation of the present disclosure.

It should be appreciated that in the foregoing description of exemplary embodiments of the disclosure, various features of the disclosure are sometimes grouped together in a single embodiment, figure, or description thereof for the purpose of streamlining the disclosure and aiding in the understanding of one or more of the various aspects. This method of disclosure, however, is not to be interpreted as reflecting an intention that an embodiment requires more features than are expressly recited in each claim. Rather, inventive aspects lie in less than all features of a single foregoing disclosed embodiment, and each embodiment described herein may contain more than one inventive feature.

It will be understood by those skilled in the art that various changes in the form and details may be made from the embodiments shown and described without departing from the spirit and scope of the disclosure.

We claim:

1. A process for testing for structural flaws in sapphire parts used in the manufacturing of electronic devices, comprising:
   transmitting a destructive acoustic signal including a Rayleigh wave onto a sapphire part; and
   determining whether the sapphire part mechanically failed in response to the transmitting of the destructive acoustic signal.

2. The process of claim 1, wherein the determining whether the sapphire part mechanically failed further comprises at least one of:
- determining whether the destructive acoustic signal breaks the sapphire part; and
- determining whether the destructive acoustic signal creates a surface flaw in the sapphire part larger than a specified size.

3. The process of claim 2, wherein the specified size of the surface flaw in the sapphire part is dependent on at least one of:
- a size of the sapphire part;
- a desired strength of the sapphire part; and
- a desired robustness of the sapphire part.

4. The process of claim 2, wherein the determining whether the sapphire part mechanically failed in response to the destructive signal further comprises determining whether the surface flaw is larger than a sub-micron in size.

5. The process of claim 1, further comprising, in response to determining that the sapphire part mechanically failed, discarding the sapphire part.

6. The process of claim 1, wherein the sapphire part is configured to be used as a cover plate for a display of the electronic device.

7. The process of claim 1, wherein the electronic device is a mobile phone.

8. The process of claim 2, wherein the Rayleigh wave has a frequency in the range of about 50 kHz to 2 GHz.

9. The process of claim 1, wherein:
- the process further comprises submerging the sapphire part in a liquid; and
- the operation of transmitting the destructive acoustic signal onto the sapphire part is performed while the sapphire part is submerged.

10. The process of claim 1, wherein:
- the sapphire part is a cover plate for an electronic device;
- the cover plate defines at least one opening therethrough; and
- transmitting the destructive acoustic signal onto the sapphire part comprises transmitting the destructive acoustic signal at a portion of the cover plate adjacent the opening.

11. A process for manufacturing an electronic device, comprising:
- generating and transmitting a destructive Rayleigh wave onto a sapphire part;
- determining whether the sapphire part mechanically failed in response to the transmitting of the destructive Rayleigh wave; and
- in response to determining the sapphire part did not mechanically fail, forming the electronic device using the sapphire part.

12. The process of claim 11, wherein the forming of the electronic device using the sapphire part further comprises forming a mobile phone as the electronic device.

13. The process of claim 11, wherein the determining whether the sapphire part mechanically failed in response to the transmitting of the destructive Rayleigh wave further comprises:
- performing a visual inspection of the sapphire part at least one of during, or after, the transmitting of the destructive Rayleigh wave onto the sapphire part; and
- determining if a surface flaw is larger than a specified flaw size of the sapphire part.

14. The process of claim 11, wherein the transmitting of the destructive Rayleigh wave onto the sapphire part further comprises directing the destructive Rayleigh wave at a specific portion of the sapphire part.

* * * * *